US010243316B2

United States Patent
Couderc et al.

(10) Patent No.: US 10,243,316 B2
(45) Date of Patent: Mar. 26, 2019

(54) METHOD AND DEVICE FOR TRIGGERING PULSED LIGHT SOURCES

(71) Applicants: HORIBA ABX SAS, Montpellier (FR); UNIVERSITE DE LIMOGES, Limoges (FR); CENTRE NATIONAL DE LA RECHERCHE SCIENTIFIQUE, Paris (FR)

(72) Inventors: Vincent Couderc, Verneuil sur Vienne (FR); Roland Grando, Saint Gely du Fesc (FR); Alexis Labruyere, Limoges (FR); Nelly Rongeat, Grabels (FR); Denisa Subtirelu, Montpellier (FR)

(73) Assignees: HORIBA ABX SAS, Montpellier (FR); UNIVERSITE DE LIMOGES, Limoges (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 15/563,420

(22) PCT Filed: Mar. 30, 2016

(86) PCT No.: PCT/EP2016/056957
§ 371 (c)(1),
(2) Date: Sep. 29, 2017

(87) PCT Pub. No.: WO2016/156429
PCT Pub. Date: Oct. 6, 2016

(65) Prior Publication Data
US 2018/0090906 A1    Mar. 29, 2018

(30) Foreign Application Priority Data

Mar. 30, 2015 (FR) .................... 15 52661

(51) Int. Cl.
*H01S 3/10* (2006.01)
*G01N 15/14* (2006.01)
(Continued)

(52) U.S. Cl.
CPC ..... *H01S 3/10046* (2013.01); *G01N 15/1031* (2013.01); *G01N 15/1427* (2013.01); *G01N 15/1459* (2013.01); *H01S 3/1024* (2013.01)

(58) Field of Classification Search
CPC .......... G01N 15/1427; G01N 15/1459; G01N 15/1031; H01S 3/1024; H01S 3/10046
See application file for complete search history.

(56) References Cited

U.S. PATENT DOCUMENTS 4,942,293 A * 7/1990 Koishi ................. H01J 31/502
250/214 VT
5,866,897 A * 2/1999 Nishizawa ........... G04F 13/026
250/214 VT
(Continued)

FOREIGN PATENT DOCUMENTS

EP     0435166 A2    7/1991
EP     1696522 A2    8/2006
(Continued)

OTHER PUBLICATIONS

International Search Report issued in International Patent Application No. PCT/EP2016/056957, dated Jun. 20, 2016 (3 pages).

*Primary Examiner* — Sang H Nguyen
(74) *Attorney, Agent, or Firm* — Arent Fox LLP

(57) ABSTRACT

The invention relates to a method for triggering a pulsed light source, wherein it comprises at least one iteration of the following steps: receiving a control signal; determining what is called a separation time between the reception of said control signal and at least one preceding control signal; adjusting at least one control parameter of said pulsed light source depending at least on said separation; generating at
(Continued)

least one electrical signal for triggering the pulsed light source depending on said at least one control parameter adjusted during the preceding step; and triggering the pulsed light source depending on said at least one triggering electrical signal.

14 Claims, 4 Drawing Sheets

(51) Int. Cl.
  *G01N 15/10* (2006.01)
  *H01S 3/102* (2006.01)

(56) References Cited

U.S. PATENT DOCUMENTS

| | | | | |
|---|---|---|---|---|
| 5,990,944 | A * | 11/1999 | Abe | H01J 31/502 |
| | | | | 250/214 VT |
| 5,995,213 | A * | 11/1999 | Davis | G01M 11/0207 |
| | | | | 356/124 |
| 6,038,240 | A | 3/2000 | Deutsch et al. | |
| 6,819,411 | B1 * | 11/2004 | Sharpe | G01N 15/1436 |
| | | | | 250/461.2 |
| 7,909,768 | B1 * | 3/2011 | Turcott | A61B 5/1455 |
| | | | | 600/481 |
| 2004/0004987 | A1 * | 1/2004 | Desor | H01S 3/097 |
| | | | | 372/57 |
| 2007/0085996 | A1 * | 4/2007 | Mangan | A61M 1/3693 |
| | | | | 356/39 |
| 2011/0019513 | A1 | 1/2011 | Ishimoto et al. | |
| 2011/0182306 | A1 * | 7/2011 | Hosseini | H01S 3/235 |
| | | | | 372/25 |
| 2013/0316440 | A1 * | 11/2013 | Rongeat | G01N 15/1031 |
| | | | | 435/287.2 |
| 2013/0328504 | A1 * | 12/2013 | Yavor | H05B 33/0815 |
| | | | | 315/307 |
| 2014/0218791 | A1 | 8/2014 | Desbiens et al. | |

FOREIGN PATENT DOCUMENTS

| | | |
|---|---|---|
| FR | 2970334 A1 | 7/2012 |
| GB | 2497549 A | 6/2013 |

\* cited by examiner

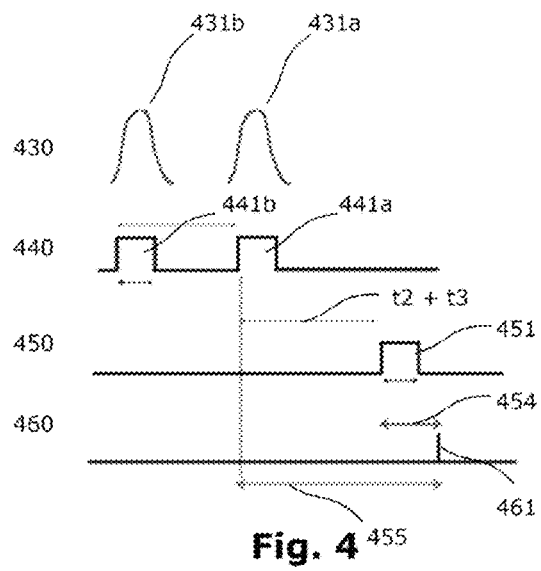
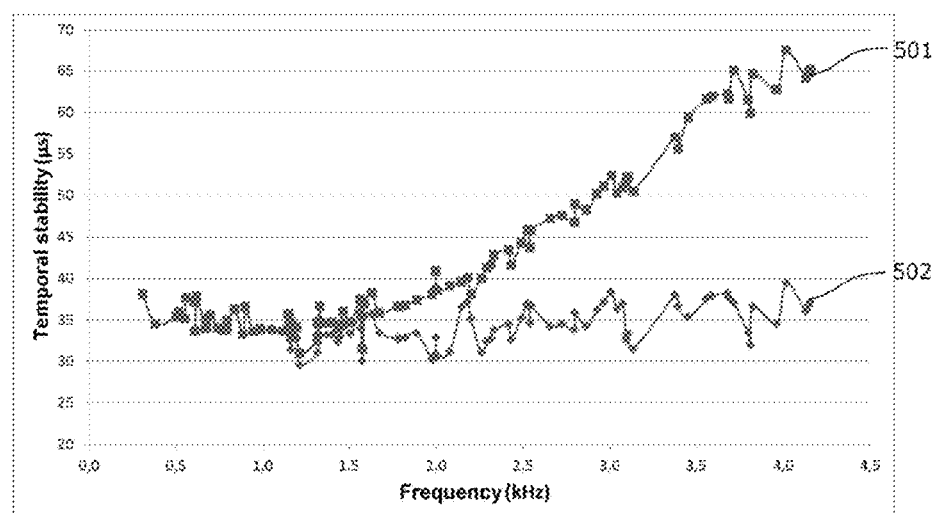
Fig. 4
Fig. 5

METHOD AND DEVICE FOR TRIGGERING PULSED LIGHT SOURCES

CROSS REFERENCE TO RELATED APPLICATIONS

This application is a 35 U.S.C. 371 National Phase of PCT Application No. PCT/EP2016/056957 filed Mar. 30, 2016, which claims benefit to FR Application No. 1552661 filed Mar. 30, 2015, the disclosure which is hereby incorporated by reference in its entirety.

TECHNICAL FIELD

The present invention relates to a method and device for triggering pulsed light sources, and in particular the applications thereof in the field of flow cytometry.

The present invention relates to the field of devices for triggering pulsed light sources, and more particularly to the field of instrumentation associated with flow cytometry.

PRIOR ART

Pulsed laser sources triggered by passive and/or active routes exhibit uncertainty on the arrival time of the delivered pulse. There exists both variability in the frequency of the light pulse from the source during recurrent operation (fixed trigger frequency) and variability in the time of light emission with respect to the command for the light source to be triggered by an external element (random trigger frequency).

Actively triggered laser sources (for example the "HELIOS" coherent source) are known which deliver sub-nanosecond pulses with a time variation with respect to the command of less than 5 ns. Unfortunately, the amplitude of the pulse generated by this type of source fluctuates greatly with the frequency of recurrence, which is highly disadvantageous for applications in the field of frequency conversions (continuum generation, frequency doubling, tripling). In the field of flow cytometry, variability in laser amplitude affects the amplitude of the optical signal characteristic of the element to be analyzed, and thus decreases the accuracy of the measurement.

Passively triggered laser sources may be controlled by temporal control of the pump wave thereof. The activation thereof then allows a laser pulse to be obtained as output with a delay that fluctuates according to the frequency of recurrence of the command. "Pulse creation delay" (PCD) and temporal jitter are then spoken of.

Documents US2008/0247425 and FR2947108 are known in particular, which describe passively triggered micro-lasers exhibiting a variation in the time delay that is too large for pulses of $10^{-9}$ seconds.

In many scientific applications, the implementation of pulsed light sources requires control over the variability in the creation time of the pulse and/or the variability in the intensity of the pulses according to the trigger frequency of said pulsed light sources; however, neither of the preceding documents addresses the technical problem of controlling the variation in the creation time of the pulse and/or controlling the variation in the amplitude of the light pulses.

The object of the present invention is to address at least the majority of the preceding problems and in addition to lead to other advantages.

One aim of the invention is to propose a method and an electronic device decreasing the temporal variability of the trigger time and the variability in the amplitude of the light pulse from a pulsed light source.

Another aim of the invention is to make the generation of a light pulse more reliable.

Another aim of the invention is to propose a flow cytometry device minimizing the probability of measuring doublets of particles.

SUMMARY OF THE INVENTION

At least one of the aforementioned objectives is obtained with a method for triggering, at a desired time, a pulsed light source comprising at least one iteration of the following steps:
  receiving a control signal;
  determining a duration, referred to as an interval, between receiving said control signal and at least one preceding control signal;
  adjusting at least one control parameter of said pulsed light source at least on the basis of said interval;
  generating at least one electrical signal for triggering the pulsed light source on the basis of said at least one control parameter adjusted during the preceding step;
  triggering the pulsed light source on the basis of said at least one electrical trigger signal.

The term "pulsed light source" is understood to mean a temporally discontinuous light source.

The control parameters of the light source comprise, in a non-limiting manner, both parameters associated with an electrical signal for controlling (period, delay, frequency, etc.) and/or an electrical signal for biasing a laser source (bias voltage), and parameters associated with the emitted light pulse (emission frequency, intensity, amplitude, pause, etc.).

The improvement in triggering the light source consists in particular in minimizing the temporal variation in the emission of the optical pulse and/or in stabilizing the amplitude of said light pulse.

In general, the control parameters of the pulsed light source correspond to all of the components that have an impact on the emission of the light pulse and/or on the quality and the shape of the emission itself.

Thus, the method according to the invention makes it possible to make triggering a pulsed light source more accurate, by decreasing both the trigger variability and the characteristics of the emission itself. Specifically, by taking into account the various parameters that interfere with the emission of the light pulse from said source, the method according to the invention allows at least one electrical trigger signal to be generated, which signal is adapted and compensated on the basis of said parameters. The electrical trigger signal thus compensated allows a light pulse to be generated, the intrinsic emission properties of which (luminous intensity, emission time, etc.) are better controlled with respect to the external trigger signal and fluctuate less with repeated and random use of said source.

The method according to the invention thus makes it possible to make the transmission of an electrical signal for controlling a pulsed light source more reliable since it is modulated on the basis of parameters associated with the operation of said source. More particularly, the amplitude of the light emission emitted by the pulsed source may thus be regulated according to at least one preceding firing.

Preferably, the method and the device that are the subject matter of the present invention in particular allow both the time of transmission of an electrical control signal and the intensity of an optical pulsed emission to be controlled on the basis of multiple prior uses of said method. More particularly, the method and the device that are the subject matter of the present invention determine a duration, referred to as an interval, on the basis of the duration separating multiple prior uses of said method and/or device.

This interval may be determined simply by calculating the arithmetic mean of the durations separating two consecutive uses and/or by way of a particular mathematical law applied to the durations separating two consecutive prior uses, while considering multiple prior uses.

Alternatively, the method and the device that are the subject matter of the present invention in particular allow both the time of transmission of an electrical control signal and the intensity of a pulsed light emission to be controlled on the basis of the immediately prior use of said method. In this case, the duration, referred to as the interval, determined by said method is determined on the basis of the reception of the current control signal and the reception of the preceding control signal.

The method according to the invention may be used in a very large number of scientific applications and measuring instruments, including flow cytometry. In particular, it makes it possible both to improve the synchronism of the light pulse implemented in said measuring instrument with a particle, and it makes it possible to improve the optical measurement taken using a pulsed light source on the basis of preceding physical measurements. The method according to the invention is not limited to one particular field of application, nor even to one particular type of instrument or measurement.

Preferably, the step of compensating for at least one control parameter of the method according to the invention may comprise at least one iteration of the following steps:
  determining, on the basis of at least one interval, a value of a delay in triggering said light source associated with said interval;
  determining a pause duration before triggering said light source on the basis of said delay value and said desired time.

Thus, the method according to the invention makes it possible to trigger the light source on the basis of the interval separating at least two consecutive control signals, stated otherwise on the basis of the average trigger frequency of the light source. As explained above, this average frequency (or average duration between two consecutive uses) may be determined on the basis of the immediately prior use of said source or obtained by determining an average (or another mathematical law) across multiple prior uses of said source.

Thus, the method according to the invention makes it possible to take into account, for a given pulsed light source, durations that are intrinsic to the latter and that vary with the trigger frequency of the light source.

Furthermore, it is also possible, using the present invention, to better control the intensity of the light pulse by parameterizing said light source on the basis of the prior use thereof.

Thus, the triggering of the light source is more accurate and more reliable since it takes into account and removes both variations in the durations that are intrinsic to the light source and in the amplitude of the light pulse during the triggering thereof. Moreover, the method according to the invention decreases, or even cancels out, the variability in time and in amplitude linked to triggering the light source on the basis of the trigger frequency or frequencies of said light source.

Advantageously, the trigger delay value may be a value predetermined on the basis of said interval. Such a delay value may be determined during prior test measurements, carried out on the source used.

Preferably, the method according to the invention may comprise a prior phase in which one or more trigger delay values may be determined for one or more interval, or frequency, values, or ranges of values, for triggering the light source.

The predetermined trigger delay values may additionally be stored in a database or a storage means in association with the values, or the ranges of values, relating to the trigger interval and/or to the trigger frequency.

Alternatively, in the prior phase, one or more mathematical relationships linking the trigger delay value to the value of the interval, or of the trigger frequency, may be determined.

According to another advantageous feature, the method according to the invention may include a step of reading, from a database, the value of said trigger delay on the basis of the value of the trigger interval. The database may be set up by means of calibration, by recording a look-up table of correspondence between a trigger delay and the one or more intervals, and/or the one or more trigger frequencies of said light source, said intervals and/or said trigger frequencies potentially varying across the entire usage range of the light source.

According to another variant of the invention, the step of adjusting at least one control parameter of the pulsed light source may additionally comprise a step of determining, on the basis of said interval, a bias voltage of said pulsed light source.

Thus, the method according to the invention makes it possible to adjust the bias voltage of the pump diode on the basis of the trigger frequency of the pulsed light source, thus making it possible to better control the luminous intensity of said source for each triggering operation. The variability in the intensity of the pulsed light source linked to the trigger frequency is thus decreased.

Preferably, the value of the bias voltage of the pulsed light source may be a value predetermined on the basis of said interval.

Also advantageously, the method according to the invention may additionally comprise a step of reading, from a database, the bias voltage of the pulsed light source.

According to another aspect, the invention relates to a method for triggering a pulsed light source of a flow cytometer comprising:
  a first inspection module capable of measuring at least one physical characteristic (for example electrical, magnetic or optical);
  a second inspection module, interacting with said pulsed light source, for measuring at least one optical characteristic using the pulsed light source,
said method being able to implement the following steps:
  measuring at least one physical quantity by the first inspection module; and
  if the value measured by the first inspection module is higher than or equal to a predetermined threshold value, the pulsed light source of the second inspection module is triggered according to any one of the embodiments of the invention.

According to yet another advantageous feature of the method for triggering a pulsed light source according to the invention, the desired trigger time may be determined on the basis of the time of reception of the detection signal and of a duration, referred to as the flow duration, determined on the basis of a distance between the first inspection module and the second inspection module, and/or a flow rate between said first inspection module and said second inspection module. Thus, it is possible to synchronize the triggering of the light source on the basis of said flow.

According to another aspect of the invention, an electronic device is proposed that comprises means arranged so as to implement all of the steps of the method according to the invention.

According to another aspect of the invention, an electronically controlled light source is proposed that comprises:
- means arranged so as to implement all of the steps of the method according to the invention; or
- a device according to the invention.

Thus, the triggered light source according to the invention is capable of calculating, in real time, a time delay of the control signal on the basis in particular of prior operations of triggering said light source. Since the frequency of prior triggering operations disrupts the time of generation of the luminous radiation, the introduction of a time delay defined on the basis of preceding triggering operations thus makes it possible to minimize variability in the time of light emission. The latter is therefore less random and more deterministic.

According to a first embodiment of the invention, the electronically controlled light source may be a laser light source.

Alternatively or additionally, the electronically controlled light source may be a pulsed light source.

Preferably, the light source may be a pulsed supercontinuum laser source.

According to yet another aspect of the invention, the invention proposes a flow cytometer comprising:
- a flow channel suitable for enabling the flow of a fluid including suspended particles;
- a first inspection module positioned at a first region and capable of measuring at least one physical characteristic of at least one particle suspended in the fluid flowing through said first region;
- a second inspection module positioned at a second region and capable of measuring at least one optical characteristic of at least one particle suspended in the fluid flowing through said second region;
- a pulsed light source for illuminating said second region for the purpose of measuring said at least one optical characteristic, the flow cytometer according to the invention being additionally able to comprise means arranged so as to implement all of the steps of the method according to the invention and/or at least one electronic device according to the invention and configured to trigger a pulsed light source. It is thus possible to control the triggering of the pulsed light source on the basis of the use thereof and with a higher degree of temporal accuracy with respect to the trigger time.

According to yet another aspect of the invention, the invention proposes a flow cytometer comprising:
- a flow channel suitable for enabling the flow of a fluid including suspended particles;
- a first inspection module positioned at a first region of said flow channel and capable of measuring at least one physical characteristic of at least one particle suspended in the fluid flowing through said first region;
- a second inspection module positioned at a second region and capable of measuring at least one optical characteristic of at least one particle suspended in the fluid flowing through said second region; and
- the flow cytometer according to the invention additionally being able to comprise a pulsed light source according to the invention for illuminating said second region for the purpose of measuring said at least one optical characteristic.

Advantageously, in the flow cytometer according to the present invention, the pause duration of the light source may be additionally defined on the basis of the time of travel of the suspended particles between the first inspection module and the second inspection module. In this way, the triggering of at least one optical measurement at the second inspection module is further synchronized with the flow of said suspended particles. It is possible to decrease the dimensions of the optical window through which the optical measurements are taken, and hence to minimize the probability of measuring doublets of particles.

Lastly, according to a last embodiment of the invention, the second inspection module (24) may be arranged so as to measure at least the light diffused and/or absorbed and/or emitted by the particles to be analyzed that are suspended in said fluid flowing through said second region (26).

DESCRIPTION OF THE FIGURES AND EMBODIMENTS

Other features and advantages of the invention will be further disclosed in the description that follows, and in several embodiments provided as non-limiting examples with reference to the appended schematic drawings, in which.

Figure 3:
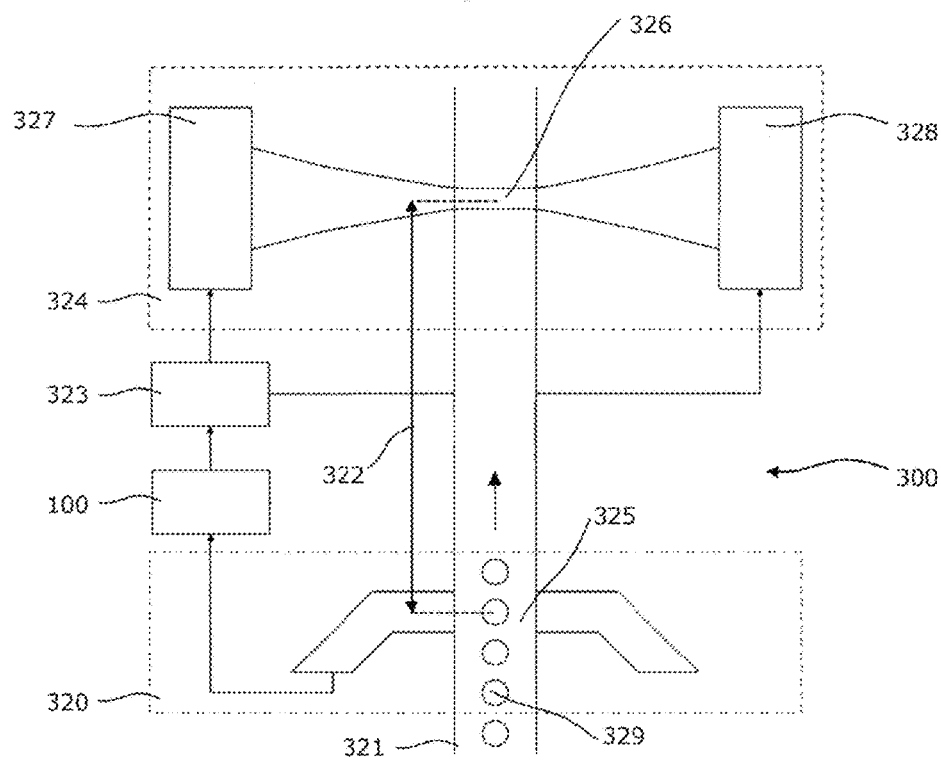
Figure 6:
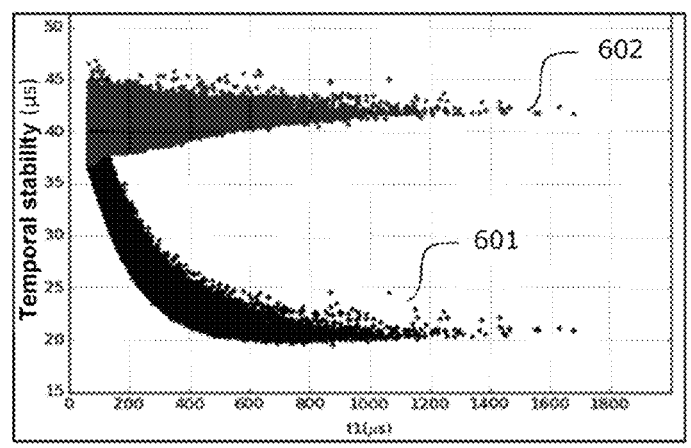

FIG. 3 schematically illustrates a flow cytometry system according to the present invention, composed of two inspection modules and incorporating an electronic device according to the invention;

FIG. 4 illustrates a timing diagram of a method for triggering the supercontinuum laser source of a flow cytometer;

FIG. 5 is a graph illustrating the levels of performance in the triggering of a light source according to the present invention;

FIG. 6 is a graph illustrating the regulation of the intensity of the light pulse according to the device of the invention.

Since these embodiments are in no way limiting, it is possible to consider, in particular, variants of the invention comprising only a selection of the features described hereinbelow in isolation (even if this selection is isolated within a sentence comprising other features), if this selection of features is sufficient to confer a technical advantage or to differentiate the invention from the prior art. This selection comprises at least one feature, preferably a functional feature without structural details, and/or with only a portion of the structural details if this portion alone is sufficient to confer a technical advantage or to differentiate the invention from the prior art.

In particular, all of the variants and all of the embodiments described can be combined with each other provided nothing prevents such a combination on a technical level.

In the figures, the parts common to more than one figure have been given the same reference number.

The principle inherent to the invention is both the triggering of the light source while taking into account a variable value corresponding to the delay generally observed for a given trigger frequency and the parameterizing of the bias of said light source on the basis of prior uses in order to control the luminous intensity of the emitted pulse. In order to achieve this, the invention consists of a method for triggering a light source at a predefined time and calculated on the basis of variable parameters such as the PCD and/or the jitter and/or the time of migration between the first inspection module and the second inspection module in the case of use in cytometry. Furthermore, these parameters depend simultaneously on the light source, on the use thereof and on the instrumentation in which it is integrated.

The method proposes carrying out at least one iteration of the following steps:
  receiving a control signal used to trigger a light source;
  determining the duration, referred to as the trigger interval, that has elapsed between the reception of said control signal and a preceding control signal, this interval being the cause of unpredictable variations in the time of emission of the light pulse in the case of a pulsed source;
  determining a value of the delay in triggering said light source on the basis of said interval and by virtue of a look-up table and/or a mathematical formula and/or by prior calibration of said light source;
  optionally, adding additional corrective terms—constants or variables—in order to determine a delay before triggering said light source on the basis of said delay value and of said desired time;
  pausing the control signal on the basis of said delay thus calculated; and
  generating an electrical trigger signal at the end of said pause step.

Figure 1:
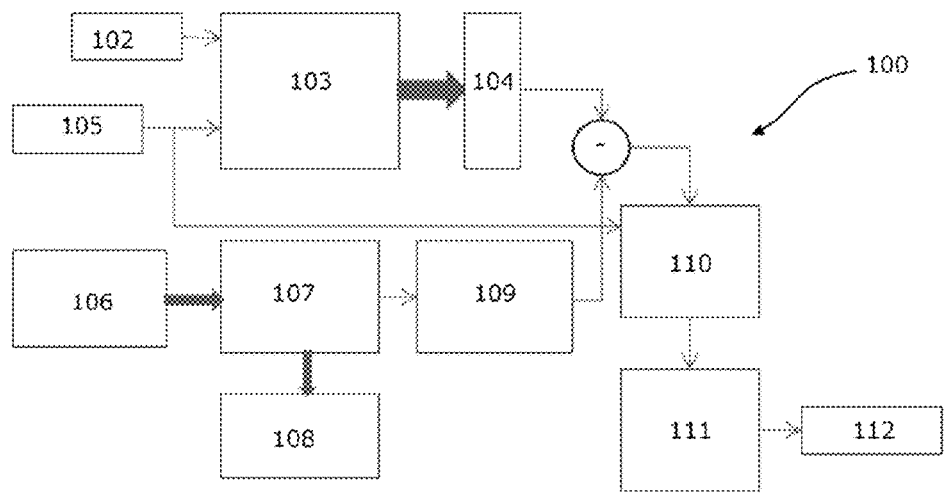
FIG. 1 illustrates a block diagram of one example of an electronic device according to the invention.

FIG. 1 illustrates a block diagram of one example of an electronic device 100 for triggering a light source at a desired time according to one embodiment of the invention.

The electronic device 100 is referred to as hereinafter as the electronic pre-compensation device.

The device 100 shown in FIG. 1 comprises storage 103 in which trigger delay values t3 for a wide frequency range, for example from a few hertz to multiple kilohertz, are recorded. For each trigger interval value, also referred to as frequency in the remainder of the application, there is a corresponding trigger delay value t3. These trigger delay values depend on the light source under consideration and are recorded in the storage 103 of the electronic pre-compensation device 100 during a prior calibration of the light source.

The trigger delay values t3 are one of the temporal components that are determined and used by the present invention to define a pause duration before triggering the light source. The calibration in question may consist, for example, in measuring the time between the emission of the signal for controlling the light source and the occurrence of the corresponding light pulse.

Alternatively, a mathematical model may be set up in order to define the value of the time delay on the basis of the trigger frequency of said light source. Depending on the application, it is optionally possible to add other temporal parameters to this time in order to complete the calibration.

Alternatively, this database or this mathematical model making it possible to determine the delay to be applied may be systematically updated in real time during the use of the overall system.

An internal clock 102 provides timing for all of the operations. For example, and in a non-limiting manner, the frequency of the clock may be 48 MHz. In general, it is preferable for the frequency of the clock to be higher than the frequency of the events that cause the light source to be triggered.

The input signals 105 correspond to the events that cause the light source to be triggered. For each trigger event there is a corresponding TTL signal.

The storage 103 thus records each trigger event and the frequency of recurrence of these events is determined. On the basis of the look-up table and/or of the mathematical model defined by calibrating the light source, the trigger delay value t3 to be applied is determined by the control unit 104 by reading from the storage 103. The control unit 104 corresponds to any type of processor.

Optionally, an offset t2 may be added to this trigger delay value t3 in order to take into account other parameters that are extrinsic or intrinsic to the light source and in order to determine the pause duration to be applied.

The value of this offset may be defined using incrementation means 106 which may be, for example, pushbuttons. Display means 108 comprising conversion logic elements 107 allow the user to view the value of the offset t2 that has been configured.

The offset t2 thus parameterized is next converted to a format compatible with that of t3, using a conversion module 109.

The offset t2 is next added to the trigger delay value t3 in the summation unit 110 and an electrical signal 111 is shaped, for example into a TTL signal or into a segment the amplitude of which is between 3.5 V and 5 V over a width of 10 µs. The shape of the electrical signal thus shaped and described here is not limiting.

Thus, the electronic pre-compensation device 100 is capable of stimulating the emission of the light source that it controls by transmitting an electrical signal 112, the temporal delay of which with respect to the input signal is at least dependent on the frequency of occurrence of an input signal.

The present invention most fully applies to all devices incorporating a triggered light source, the triggering of which depends on at least one detectable external event. For example, but in a non-limiting manner, the electronic pre-compensation device according to the present invention may consist of an electronic circuit board incorporated in a triggered or independent light source; and it may preferably be used in flow cytometers, in sensor systems, in laser remote detection (lidar) systems, etc.

Figure 2A:
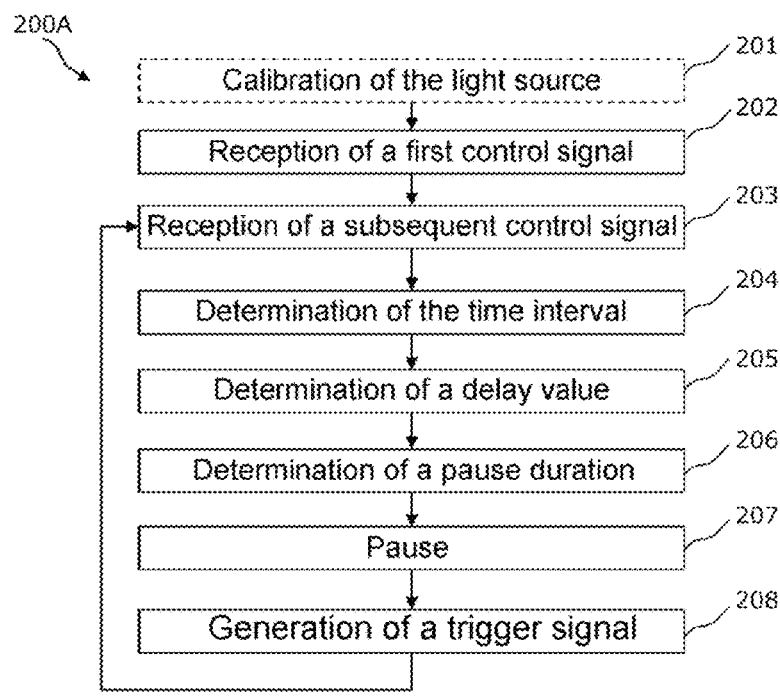
FIG. 2A is a representation of one example of a method for triggering a pulsed light source according to the present invention and of which the emission time is controlled.
Figure 2B:
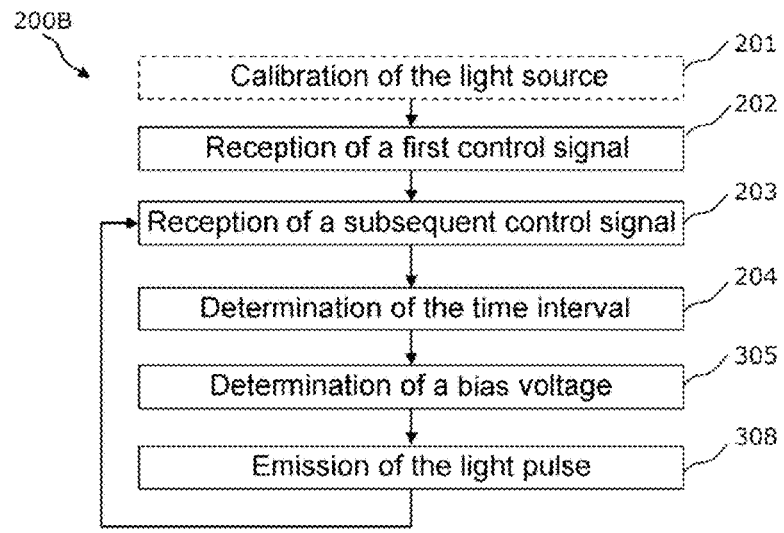
FIG. 2B is a representation of one example of a method for triggering a pulsed light source according to the present invention and of which the luminous intensity is controlled.

With reference to FIGS. 2A and 2B, two particular embodiments of the method according to the invention will now be described.

FIG. 2A is a representation of one example of a method for triggering a pulsed light source, the transmission time of which is controlled, while FIG. 2B illustrates a method for triggering a light source, the intensity of the optical pulse of which is controlled.

Methods 200A and 200B shown in FIGS. 2A and 2B, respectively, comprise an optional first step of calibrating 201 the light source in order to determine the intrinsic temporal characteristics of the triggering of the source. This step 201 comprises, for example, determining the average response time of said light source on the basis of the trigger frequency: for each frequency or frequency range, the response time is measured and recorded in a storage zone in order to make it possible, in later steps of the method 200A, to determine the pause. Step 201 may also consist in calibrating the luminous intensity of the pulsed source on the basis of the trigger frequency: for each frequency or range of frequencies, the bias voltage required to obtain a given luminous intensity is recorded in a storage zone in order to make it possible, in later steps of the method 200B, to determine the bias voltage required by said source or by an auxiliary source having the same function.

Alternatively, the calibration 201 of the light source may consist in determining a regression function linking the response time to the trigger frequency.

Once the calibration step 201 has been carried out, the following steps are carried out.

A first control signal is received in a step 202. It may come from any device with which the light source is interacting. More particularly, this may be a device outside the light source, such as an inspection module for example, being used to synchronize the light source. This may also be a device inside the light source such as an internal clock for example.

The following step of the method that is the subject of the invention consists of another step of receiving a subsequent control signal 202. Preferably, the subsequent control signal has the same origin as the first received control signal. However, the light source and the trigger method according to the invention are not limited to a single origin and a plurality of trigger sources for said light source may be envisaged without departing from the scope of the invention.

Next, a step 204 allows the exact duration that has elapsed between the two control signals to be determined.

Alternatively, as described in the preceding paragraphs, the duration calculated in step 204 may be obtained by taking into account a plurality of preceding control signals, and by calculating an arithmetic mean or any other mathematical law on the basis of the duration separating the reception of two successive control signals.

In the method illustrated in FIG. 2A, this duration is subsequently used in a step 205 for determining the value of the trigger delay to be associated with this duration. This trigger delay value may be determined in any manner without departing from the scope of the present invention. The value of the trigger delay is either read from storage in which it was stored in the calibration step, or determined on the basis of a mathematical relationship determined in the calibration step. The following step 206 consists in determining the pause duration that will be applied to the light source. This pause duration takes into account the trigger delay value determined in the preceding step but may also include other parameters for the purpose of modulating this delay value with constant, variable or statistical parameters so as to take into account other influences outside or inside the light source. In particular, in the context of use in a flow cytometer, it is possible to add, to the value of the delay obtained in step 205, a temporal component corresponding to the time of migration of the particles between the two inspection modules of the flow cytometer.

Step 207 consists of a pause, the duration of which is equal to that determined in step 206.

Lastly, a trigger signal is transmitted in step 208 in order to trigger the light source.

The method is iterative and repeated from step 202 when a new control signal is received.

In the method illustrated in FIG. 2B, the duration calculated in step 204 makes it possible to determine a bias voltage 305 required to obtain the desired luminous intensity of the pulse emitted by the pulsed source. This bias voltage may be determined in any manner without departing from the scope of the present invention: it may be read from storage in which it was stored in the calibration step 201, or else determined on the basis of a mathematical relationship determined in the calibration step 201.

In the following step 308, the light pulse emitted by the source will thus have an intensity which will not be affected by the prior use of said source, and in particular the frequency of prior uses.

FIG. 3 schematically illustrates an example of a flow cytometry system according to the present invention.

The flow cytometry system 300 shown in FIG. 3 comprises a flow channel 321, two inspection module 320 and 324, a controller 323 and an electronic pre-compensation device, such as for example the device 100 of FIG. 1. In the example described here, the analyzed flow comprises blood cells flowing through the flow channel 321. However, it may be any type of flow comprising particles.

The flow cytometry system 300 comprises a first region 325 that is remote from a second region 326 and through which the analyzed cells 329 travel separately from one another with variable distances between them. This distance 322 may vary according to the flow cytometry systems but generally remains between a few tens of micrometers and a few hundreds of micrometers.

Assuming that the analyzed cells 329 move at constant speed, the time of travel of the analyzed cells 329 through the flow channel 321, in particular between the first region 325 and the second region 326, is constant.

The first inspection module 320 is located on either side of the first region 325 and allows an electrical characteristic of the fluid flowing through said first region 325 to be measured. In the absence of cells in the flow channel 321, the flow passing through the first region 325 defines a load impedance measured by two electrodes placed on either side of said channel. When a cell passes through the first region 325, it leads to an increase in the load impedance. This variation in impedance makes it possible in particular both to determine the volume of the cell and to carry out a cell count.

The second inspection module 324 is located at the second region 326, on either side of the flow channel 321. It allows at least one measurement of the optical characteristics of the fluid flowing through said second region 326 to be taken. It comprises at least one triggered light source 328 and at least one analysis unit 327 for the purpose of taking, for example, optical absorption, reflection, transmission and/or fluorescence measurements and characterizing physi-cochemical properties of the particles, in particular of the cells. The at least one triggered light source 328 may be a laser, a supercontinuum source or any other type of triggered source that is compatible with these analyses, in particular pulsed sources for example.

The triggering of the second inspection module 324 is regulated by a controller 323 and conditional upon the transit of a cell 329 in front of the first inspection module 320. In order to achieve this, the controller 323 receives a detection signal from the first inspection module 320 and transmits a control signal for activating the second inspection module 324.

The pre-compensation electronic device 100 of the light source 328 is intercalated between the controller 323 and the first inspection module 320. It thus makes it possible to introduce a pause duration that is determined on the basis of various parameters, which may be variable such as the PCD or jitter, and/or invariant such as the time of migration of the particles between the first inspection module and the second inspection module. In particular, these parameters may be:

the distance between the first region 325 and the second region 326;

the speed of propagation of the cells 329 through the flow channel;

the variation in the occurrence of the cells 329;
the trigger time of the light source 328.

Thus, the light source 328 is triggered at the very moment when a cell previously detected by the first inspection module 320 passes through the second region 326. Similarly, the optical analyzer 327 is controlled so as to take the measurement in synchronism with the triggering of the triggered light source 328.

In the example described in FIG. 1 and applied to the present device, the offset t2 corresponds to the time of travel of the cells 329 between the first region 325 and the second region 326. The value of the trigger delay t3 itself corresponds to the response time of the light source 328. As mentioned above, this time varies according to the trigger frequency, hence according to the frequency with which a cell 329 appears in front of the first inspection module 320.

FIG. 4 illustrates a timing diagram of the method for triggering a supercontinuum laser source of a flow cytometer. Row 430 shows a succession of signals 431a and 431b arising from the first inspection module 320. They are for example impedance measurements corresponding to the transit of two consecutive cells 329 through the flow channel 321 at the first region 325. For example, the first inspection module 320 continually measures the electrical impedance of the flow channel 321 at the first region 325. In the absence of cells, the first inspection module measures an initial impedance value, which may be noisy according to various parameters. When a cell 329 enters the first region 325, the measured impedance increases substantially beyond the noise level measured previously. A threshold value may be defined so as the discretize the presence or absence of cells 329 in the first region 325.

The measurements taken by the first inspection module are used as a control signal.

Row 440 shows a TTL signal corresponding to the impedance signal 431 and shaped by the controller 323. The width of the patterns 441a and 441b substantially corresponds to the width at half maximum of the impedance signal 431a and 431b, for example of the order of 10 µs. The two signals 441a and 441b are separated by the same duration t1 as that which separates the patterns 431a and 431b. This duration of separation t1 corresponds to the time period between the transit of two consecutive cells 329 in front of the first inspection module 320. It equally makes it possible also to define a frequency of recurrence of the cells f1=1/t1.

Row 450 shows the signal output by the controller 323 delayed by a pause duration t2+t3. Thus, the pattern 451 is a control signal for the second inspection module 324 and the optical analyzer 327, corresponding to the impedance signal 431a.

Row 460 shows the light signal output by the triggered light source 328. In the example illustrated in FIG. 4, this is a light pulse 461 that occurs after a certain delay 454 with respect to the control signal 451 transmitted by the controller 323.

This delay 454 depends on multiple parameters that are inherent to the triggered light source 328 itself. In particular, this is the pulse creation delay (PCD), which is constant for a given trigger frequency, and the temporal jitter, which is a purely statistical parameter. Therefore, by determining the frequency of appearance f1 of the cells 329 by the transit thereof in front of the first inspection module 320, it is possible to determine the value of the trigger delay t3 to be applied to the triggering of the light source 328.

The table below illustrates an example of correlation between the trigger delay value on the basis of the duration t1 separating two consecutive transits of cells 329 in front of the first inspection module 320 and used to determine the pause duration of the method according to the invention:

TABLE 1

Look-up table of correspondence between the time period of appearance of cells in front of the first inspection module and the time correction to be applied to the triggering of the light source.

| t1(ms) | | |
|---|---|---|
| Min | Max | t3(µs) |
| 0.894 | 100.000 | 0 |
| 0.630 | 0.893 | 1.5 |
| 0.569 | 0.629 | 2.5 |
| 0.527 | 0.568 | 4 |
| 0.510 | 0.526 | 3 |
| 0.470 | 0.509 | 8 |
| 0.449 | 0.469 | 3 |
| 0.385 | 0.448 | 9 |
| 0.351 | 0.384 | 13 |
| 0.323 | 0.350 | 14 |
| 0.292 | 0.322 | 19 |
| 0.270 | 0.291 | 24 |
| 0.250 | 0.269 | 28 |

For example, for times t1 of between 0.25 ms and 0.269 ms, the value of the trigger delay t3 to be applied to the light source is 28 µs. However, if t1 is between 0.894 ms and 2 ms, the trigger delay t3 is zero.

The correlations between the trigger frequency f1 and the trigger delay f3 to be applied to the light source are obtained by calibrating the corresponding triggered light source. Thus, for each trigger frequency, or for each trigger frequency range, the average time of occurrence of the light signal obtained over multiple triggering operations is measured.

The look-up table of correspondence between the frequency of appearance F1 and trigger delay t3—such as illustrated in TABLE 1—is next recorded in the electronic pre-compensation device according to the present invention.

FIG. 5 is a graph illustrating the levels of performance in the triggering of a light source at 4.2 kHz using the present invention, as a function of the frequency of said triggering operation.

Curve 501 shows the variability in the triggering of the light source of the prior art (equivalent to reference 454), without the electronic pre-compensation device 100 according to the invention.

Curve 502 itself represents the variability in the triggering of the light source (equivalent to reference 455, where t2=0) when the electronic pre-compensation device 100 is used to control the light source 328. The measurements are taken up to 4.2 kHz. Without an electronic pre-compensation device 100, the variability 455 in the triggering of the light pulse 461 increases with frequency and reaches approximately 36.5 µs. However, by using the electronic pre-compensation device 100 according to the invention, the temporal stability of the triggering is improved and the variability in the triggering is now only 9.9 µs.

FIG. 6 is a graph illustrating the levels of performance in the triggering of a light source at 25 kHz using the present invention, as a function of the time between each electrical signal of the biological cell corresponding to the inverse of the frequency of said triggering operation.

These measurements have therefore been taken by simulating the transit of biological cells through the optical counting window. In order to increase the accuracy of the measurements and decrease the time taken to calibrate the supercontinuum lasers, the following are automatically acquired: the trigger frequency of the source, the time between the trigger signal and the laser pulse.

These measurements are subsequently processed by virtue of a computer program and a mathematical law has additionally been determined by linearizing around a reference point. Next, the integration of a pre-compensation law deduced from the preceding exponential law makes it possible to act on the obtained laser pulses.

Curve 601 shows the variability in the triggering of the light source of the prior art (equivalent to reference 454), without the electronic pre-compensation device 100 according to the invention.

Curve 602 itself represents the variability in the triggering of the light source (equivalent to reference 455, where t2=0) when the electronic pre-compensation device 100 is used to control the light source 328. The measurements are taken up to 25 kHz. Without an electronic pre-compensation device 100, the variability 455 in the triggering of the light pulse 461 increases with frequency and reaches approximately 22 μs. However, by using the electronic pre-compensation device 100 according to the invention, the temporal stability of the triggering is improved and the variability in the triggering is now only 6 μs.

The creation of this circuit board has made it possible to improve various technical points with respect to the circuit board described in example 5, such as:
decreasing the test times
being closer to the conditions of a hematology analyzer
increasing the accuracy of the measurements
increasing the accuracy of the laser pre-compensation to be applied.

Figure 7:
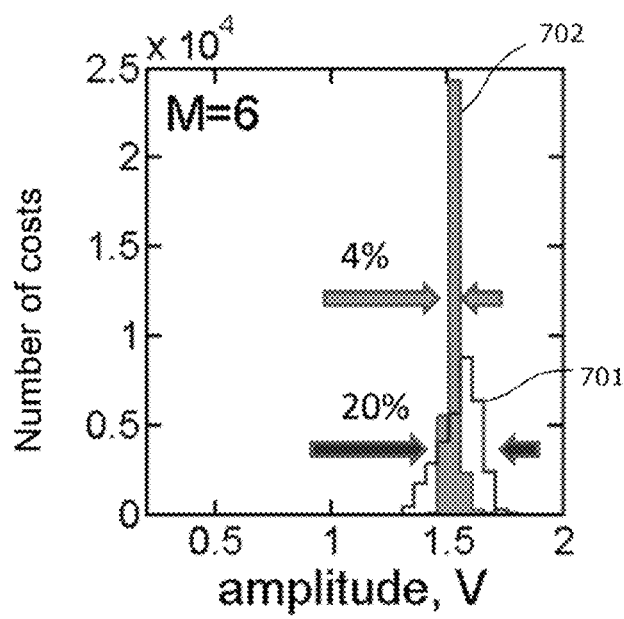

FIG. 7 is a graph showing the regulation of the intensity of the light pulse using the invention.

More particularly, FIG. 7 illustrates two histograms of the amplitude measured (in volts) by a photodiode located facing a pulsed source and representative of the luminous intensity of said source in two different situations:
a first curve 701 illustrates the variation in the luminous intensity for multiple successive firings of the pulsed light source without the amplitude compensation device according to the invention. It can thus be observed that a majority of the pulse has a measured light amplitude of 1.6 V. The distribution of the measured light amplitudes is spread between 1.3 V and 1.7 V, with a width at half maximum of the order of 20% with respect to the average measured amplitude of said pulses.
a second curve 702 illustrates the variation in the luminous intensity for multiple successive firings of the pulsed light source with the amplitude compensation device according to the invention. It can be observed that, in this case, the distribution of the measured light amplitudes has a width at half maximum of the order of 4% with respect to the average measured amplitude of said pulses.

Thus, FIG. 7 demonstrates that the device according to the invention—in any of the claimed forms thereof—makes it possible to decrease the variability in the intensity of the pulsed light source.

Of course, the invention is not limited to the examples that have just been described, it being possible for many modifications to be made to these examples without departing from the scope of the invention. More particularly, the various features, forms, variants and embodiments of the invention can be combined with one another in various combinations insofar as they are not mutually incompatible or exclusive. In particular, all of the variants and embodiments described above can be combined with one another.

The invention claimed is:

1. A method for triggering a pulsed light source in a device comprising a pulsed light source, comprising:
receiving a control signal;
determining an interval between receiving said control signal and at least one preceding control signal;
adjusting at least one control parameter of said pulsed light source at least on the basis of said interval;
generating at least one electrical signal for triggering the pulsed light source on the basis of said at least one control parameter adjusted during the preceding step; and
triggering the pulsed light source on the basis of said at least one electrical trigger signal,
wherein said receiving, determining, adjusting, generating, and triggering is performed one or more times, and
wherein said adjusting at least one control parameter of the pulsed light source comprises:
determining, on the basis of the interval, a trigger delay value associated with said interval; and
determining a pause duration before triggering said light source on the basis of said trigger delay value and a desired time,
wherein said determining a trigger delay value associated with said interval and said determining a pause duration is performed one or more times.

2. The method of claim 1, wherein the trigger delay value is a value predetermined on the basis of the interval.

3. The method of claim 1, further comprising reading, from a database, the trigger delay value.

4. The method of claim 1, wherein said adjusting at least one control parameter of the pulsed light source further comprises determining, on the basis of the interval, a bias voltage of the pulsed light source.

5. The method of claim 4, wherein the bias voltage is a value predetermined on the basis of the interval.

6. The method of claim 4, wherein the value of the bias voltage is read from a database.

7. A method for triggering a pulsed light source of a flow cytometer, said flow cytometer comprising:
a first inspection module comprising two electrodes capable of measuring at least one electrical characteristic; and
a second inspection module comprising at least one triggered light source and at least one analysis unit, interacting with said pulse light source, for measuring at least one optical characteristic using the pulsed light source,
said method comprising:
measuring at least one electrical quantity by the first inspection module; and
if the value measured by the first inspection module is higher than or equal to a predetermined threshold value, the pulsed light source of the second inspection module is triggered in accordance with the method of claim 1.

8. The method of claim 7, wherein triggering of said pulsed light source is controlled on the basis of the time of reception of the detection signal and of a flow duration determined on the basis of:
a distance between the first inspection module and the second inspection module; and
a flow rate between said first inspection module and said second inspection module.

9. An electronic device configured to perform the method of claim 1.

10. An electronically controlled pulsed light source, comprising the device of claim 9.

11. The electronically controlled pulsed light source of claim 10, comprising a supercontinuum laser source.

12. A flow cytometer comprising:
- a flow channel suitable for enabling the flow of a fluid including suspended particles;
- a first inspection module comprising two electrodes positioned at a first region of said flow channel and capable of measuring at least one physical characteristic of at least one particle suspended in the fluid flowing through said first region;
- a second inspection module comprising at least one triggered light source and at least one analysis unit positioned at a second region and capable of measuring at least one optical characteristic of at least one particle suspended in the fluid flowing through said second region; and
- the electronically controlled pulsed light source of claim 10 for illuminating said second region for the purpose of measuring said at least one optical characteristic.

13. A flow cytometer comprising:
- a flow channel suitable for enabling the flow of a fluid including suspended particles;
- a first inspection module comprising two electrodes positioned at a first region of said flow channel and capable of measuring at least one physical characteristic of at least one particle suspended in the fluid flowing through said first region;
- a second inspection module comprising at least one triggered light source and at least one analysis unit positioned at a second region and capable of measuring at least one optical characteristic of at least one particle suspended in the fluid flowing through said second region; and
- a pulsed light source for illuminating said second region for the purpose of measuring said at least one optical characteristic, wherein said flow cytometer is capable of performing the method of claim 1.

14. The flow cytometer of claim 13, wherein the second inspection module is arranged so as to measure at least the light diffused and/or absorbed and/or emitted by said fluid flowing through said second region.

* * * * *